(12) United States Patent
Watts

(10) Patent No.: US 6,908,445 B2
(45) Date of Patent: Jun. 21, 2005

(54) ANKLE-FOOT ORTHOSIS

(76) Inventor: Robert J. Watts, Venards Cottage, North Gorley, Fordingbridge, Hampshire (GB), SP6 2PJ ( * ) Notice: Subject to any disclaimer, the term of this patent is extended or adjusted under 35 U.S.C. 154(b) by 6 days.

(21) Appl. No.: 09/529,482

(22) PCT Filed: Oct. 12, 1998

(86) PCT No.: PCT/GB98/03068
§ 371 (c)(1),
(2), (4) Date: Jun. 19, 2000

(87) PCT Pub. No.: WO99/18896
PCT Pub. Date: Apr. 22, 1999

(65) Prior Publication Data
US 2003/0153862 A1 Aug. 14, 2003

(30) Foreign Application Priority Data
Oct. 15, 1997 (GB) .............................. 9721863
Jul. 7, 1998 (GB) .............................. 9814726

(51) Int. Cl.⁷ .............................................. A61F 5/00
(52) U.S. Cl. .............................. 602/28; 602/5; 602/23; 602/27
(58) Field of Search .............................. 602/5, 16, 23, 602/27–29, 6, 12; 128/882

(56) References Cited

U.S. PATENT DOCUMENTS

| | | | |
|---|---|---|---|
| 3,504,668 A | | 4/1970 | Boudon ........................ 128/80 |
| 3,589,359 A | * | 6/1971 | Hill |
| 3,976,059 A | | 8/1976 | Lonardo .................... 128/80 E |
| 4,187,844 A | * | 2/1980 | Caprio, Jr. .................... 602/65 |
| 4,559,934 A | | 12/1985 | Philipp ...................... 128/80 E |
| 4,651,723 A | | 3/1987 | Satoh ........................ 128/80 E |
| 4,862,900 A | * | 9/1989 | Hefele .......................... 602/27 |
| 4,974,343 A | * | 12/1990 | Davidson |
| 5,185,000 A | * | 2/1993 | Brandt et al. .................. 602/63 |
| 5,219,324 A | * | 6/1993 | Hall |
| 5,257,969 A | | 11/1993 | Mance ........................ 602/28 |
| 5,399,155 A | | 3/1995 | Strassburg et al. ............. 602/28 |
| 5,445,603 A | * | 8/1995 | Wilkerson .................... 602/27 |
| 5,464,384 A | | 11/1995 | Cromartie .................... 602/27 |
| 5,472,414 A | | 12/1995 | Detty .......................... 602/27 |
| 5,584,799 A | * | 12/1996 | Gray |
| 5,676,641 A | | 10/1997 | Arensdorf et al. ............. 602/27 |

FOREIGN PATENT DOCUMENTS

| | | |
|---|---|---|
| CA | 2 037 546 | 7/2002 |
| EP | 0114560 A2 | 8/1984 |
| EP | 0466100 A1 | 1/1992 |
| GB | 2188550 A | 10/1987 |
| GB | 2298140 A | 8/1996 |
| WO | WO 94/00083 | 1/1994 |
| WO | WO 94/09727 | 5/1994 |

* cited by examiner

Primary Examiner—Nicholas D. Lucchesi
Assistant Examiner—Lalita M Hamilton
(74) Attorney, Agent, or Firm—Thomas Schneck; Gina McCarthy

(57) ABSTRACT

One embodiment provides an ankle-foot orthosis (32) for resisting plantarflexion of a patient's foot, the orthosis (32) comprising: a resiliently flexible sock-like structure (34) enveloping, in use, at least a portion of a patient's lower leg in the vicinity of the ankle and at least a portion of the plantar (46) and dorsal (48) aspects of the patient's foot. Another embodiment provides an ankle-foot orthosis (1) for resisting plantarflexion of a patient's foot, the orthosis (1) comprising: a resilient rib (3) locatable, in use, along and in abutment with at least a portion of the dorsal aspect of the patient's foot and at least a portion of the patient's lower leg, the orthosis (1) comprising means (7) for securing the rib (3) to the patient's foot and lower leg.

25 Claims, 3 Drawing Sheets

ANKLE-FOOT ORTHOSIS

This invention relates to ankle-foot orthoses.

Orthoses are mechanical devices which impose forces upon a limb of a patient and can be used for a variety of different purposes. For example, orthoses may be provided for supportive, functional, corrective or protective purposes, or for a combination of these. Ankle-foot orthoses are typically provided to provide protection to the ankle and foot of a patient as well as to provide support against excessive plantarflexion or dropping of the foot. In addition to this resistive function, they may also be employed to assist dorsiflexion of the patient's foot during the push off phase of the patient's gait.

Foot plantarflexion is a medical condition that can arise from a variety of causes, for example disease or congenital abnormality. Patients affected by this condition typically experience difficulty in walking as they must lift their foot excessively from the ground in order to avoid stumbling.

A variety of different ankle-foot orthoses have previously been proposed for resisting plantarflexion, and in some cases for additionally assisting dorsiflexion. FIGS. 1a, 1b, 2a and 2b illustrate two of these previously proposed devices.

FIG. 1a illustrates one previously proposed ankle-foot orthosis before it is assembled on a patient. The orthosis 10 must be used in conjunction with a shoe 12 that provides close contact between the shoe and the foot in the region of the instep. The orthosis 10 comprises a pair of supporting metal uprights 14, one connected to either side of the shoe 12 in the region of the heel 16. The connections each comprise a plantarflexion stop 18 that resists foot drop and may also include springs (not shown) to assist dorsiflexion. The upper ends of the uprights are connected to a supporting strap 20 which is securable about the patient's calf. With reference to FIG. 1b, it can be seen that the supporting strap 20 provides support about the patient's calf, and that the plantarflexion stops 18 and shoe 12 provide support under the foot of the patient to resist plantarflexion.

FIGS. 2a and 2b illustrate another previously proposed orthosis device which must also be used in conjunction with a shoe that provides close contact between the shoe and the foot in the region of the instep. In this example, the orthosis 22 comprises a one-piece plastics moulding 24 which comprises a calf abutting region 26 and a sole abutting region 28. The top of the calf abutting region 26 is provided with a closure mechanism 27 that enables the device to be secured to the calf of a patient. The sole abutting region 28 acts in conjunction with the shoe 30 to support the foot of the patient. The stiffness of the plastics moulding and the shape thereof in the region of the ankle defines the amount of resistance to plantarflexion. If more resistance is required, then the gap across the front of the ankle can be reduced, or the stiffness of the plastics can be increased.

Both of the aforementioned previously proposed devices adequately support the foot of a patient to resist plantarflexion. However, they both exhibit serious deficiencies that make them highly unpopular with patients.

A first disadvantage is that both of the previously proposed orthoses are large bulky devices which are clearly visible when worn. Thus, the patient's illness or abnormality is immediately apparent to others and this can adversely affect the patient's state of mind. This problem can be particularly apparent with child patients as the orthosis is an immediately obvious difference which other children can ridicule. It can also be a serious problem for adult patients as a visible device immediately labels them as a disabled or abnormal person with corresponding ramifications for their personal and working lives.

A further disadvantage is that both of these previously proposed devices must be worn with shoes. Thus, if a patient wished to walk without shoes or to go swimming, for example, then they would have to do so without any means for resisting plantarflexion.

A further disadvantage is that these previously proposed devices can cause extreme discomfort when worn. This problem is particularly apparent with the orthosis of FIGS. 2a and 2b as the device extends under the foot of the patient and thus the full weight of the patient bears upon the device when the patient walks.

Yet another disadvantage is that both of these previously proposed devices are difficult and time consuming to put on and take off. Furthermore, the second device often requires the fabrication of special shoes as it is often not possible to fit the device within normal off-the-shelf shoes. Finally, both devices are expensive to make In accordance with the invention, there is provided an ankle-foot orthosis for resisting plantarflexion of a patient's foot, the orthosis comprising: a resiliently flexible sock-like silicone structure enveloping, in use, at least a portion of a patient's lower leg in the vicinity of the ankle and at least a portion of the plantar and dorsal aspects of a patient's foot.

Thus, this aspect of the invention provides a discrete arrangement which adequately resists plantarflexion without requiring the patient to wear a shoe.

Preferably the orthosis comprises a reinforcing means for further resisting planterflexion of the foot. The reinforcing means may be a length of tape, the ends of the tape being joined together to form a figure-of-eight passing under the instep, behind the ankle and crossing on the dorsal aspect of the foot. Alternatively, the reinforcing means may comprises a rib running along at least a portion of the dorsal aspect of the foot and substantially midway between the medial malleolus and the lateral malleolus. Preferably the reinforcing means has a greater resilience than the sock-like structure.

The sock-like structure may be defined by the rib and a pair of straps, one secured to either end of the rib and respectfully securable about the plantar aspect of the foot and the portion of the patient's lower leg in the vicinity of the ankle.

Preferably, the orthosis comprises an insertion slit extending midway between the medial malleolus and the lateral malleolus towards the calcaneum, means being provided to securely close the slit once the patient's foot has been inserted in the orthosis.

The closing means may comprise a mechanical hook and loop fastener, a set of hoops or hooks being provided adjacent one edge of the slit and a corresponding set of hooks or hoops being provided on a closure member affixed to the other side of the slit, respective hooks and loops being connectable to securely close the slit. Alternatively, the closing means may comprise a zip fastener secured to opposite sides of the slit. As a further alternative, the closing means may comprise a set of eyelets closable by a lace.

Preferably, the orthosis envelops the dorsal and plantar aspects of the foot without enveloping the toes. Preferably, the orthosis envelops the plantar aspect of the foot without enveloping the calcaneum. The orthosis could envelop the calcaneum if, for example, mechanical correction of the heel bone is required. The device may also be contoured on the surface abutting, in use, the plantar aspect of the foot to aid support of the metatarsals and to position the foot correctly.

Preferably, the sock-like structure is a 35 shore silicone elastomer, or a higher or lower shore silicone elastomer. Preferably, the reinforcing means is of silicone.

Preferably, the orthosis is skin coloured and/or fabricated by injection moulding. The orthosis could alternatively be brightly coloured so as to appeal to children.

In accordance with a second aspect of the invention, there is provided a kit comprising a plurality of orthoses as described herein, the orthoses being of varying size and shape for fitting to feet of different sizes and shapes. The kit may also comprise differently coloured orthoses to allow the matching of the colour of the orthosis to the skin colour of the patient.

In accordance with a further aspect of the invention, there is provided an ankle-foot orthosis for resisting plantarflexion of a patient's foot, the orthosis comprising: a resilient rib locatable, in use, along and in abutment with at least a portion of the dorsal aspect of the patient's foot and at least a portion of the patient's lower leg, the orthosis comprising means for securing the rib to the patient's foot and lower leg.

In one embodiment, the securing means comprises a first strap means securable about one end of the rib and the patient's lower leg and a shoe for securing the other end of the rib to the patient's foot.

In another embodiment, the securing means comprises a first strap means securable about one end of the rib and the patient's lower leg and a shoe for securing the other end of the rib to the patient's foot.

In another embodiment, the securing means comprises an adhesive, at least end portions of the rib being adhered to the patient's lower leg and foot.

In any event, it is preferred that the rib is of plastics, such as polypropylene or ortholene.

Preferably, the orthosis is skin coloured and/or fabricated by injection moulding. The orthosis could be formed by stamping from sheet material. The orthosis could be brightly coloured so as to appeal to children.

In accordance with another aspect of the invention, there is provided a kit comprising a plurality of orthoses as described herein, the orthoses being of varying size and shape for fitting to feet of different sizes and shapes. The kit may also comprise differently coloured orthoses to allow the matching of the colour of the orthoses to the skin colour of the patient.

Embodiments of the present invention will now be described, by way of example only, with reference to the accompanying drawings, in which.

Figure 1A:
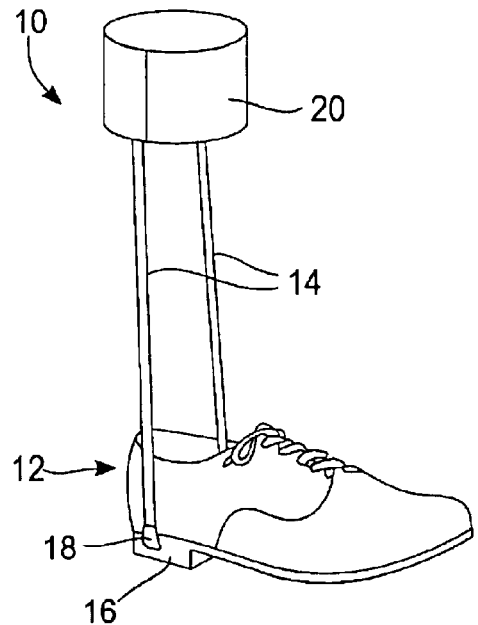
FIGS. 1a and 1b are schematic representations of one previously proposed orthosis.
Figure 1B:
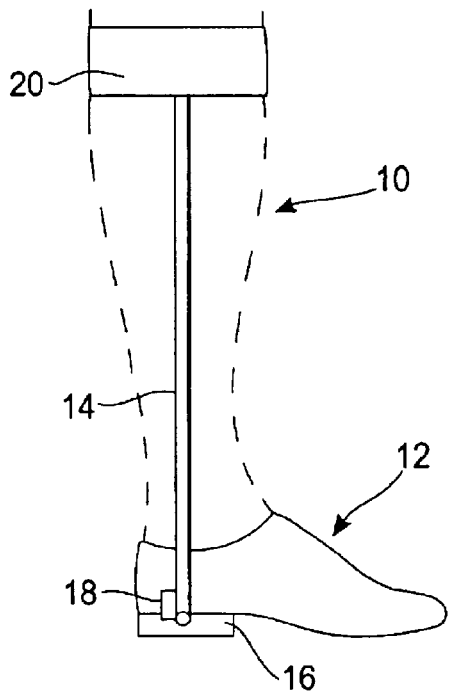
Figure 2A:
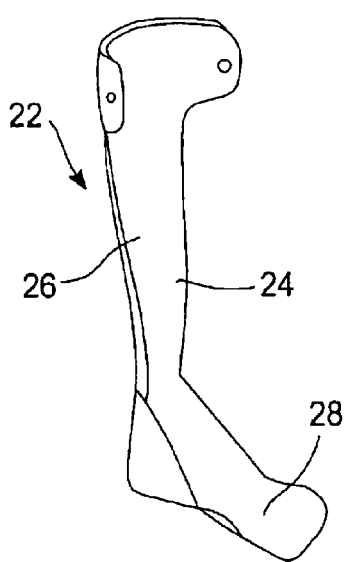
FIGS. 2a and 2b are schematic representations of another previously proposed orthosis.
Figure 2B:
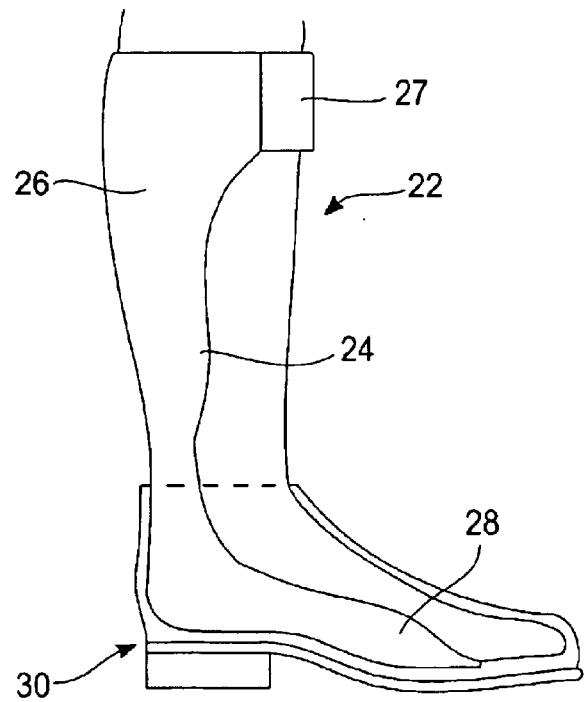
Figure 3:
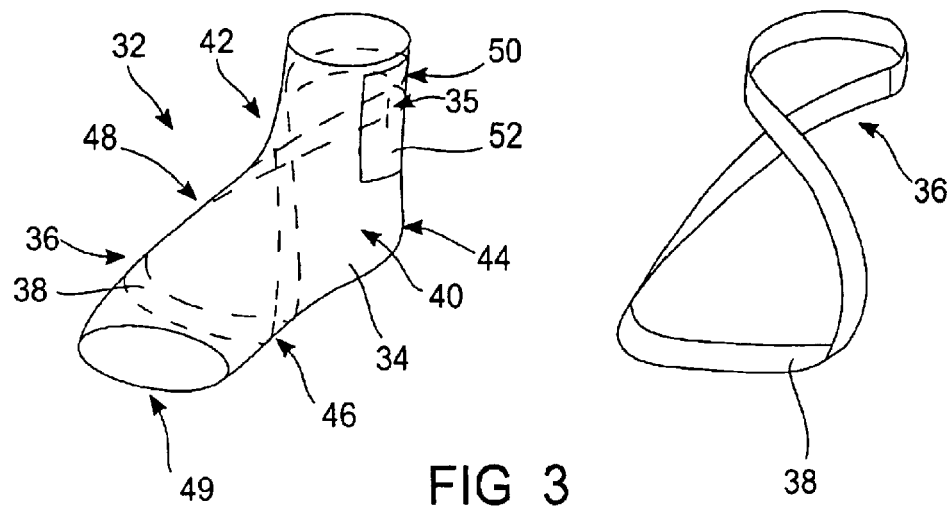
FIG. 3 is a schematic representation of an orthosis according to a first aspect of the invention.

With reference to FIG. 3, the orthosis 32 comprises a resiliently flexible sock-like structure 34 and a reinforcing means 36 (shown in ghost), which in this embodiment is a tape 38—the ends of which are joined together to form a figure-of-eight which passes under the instep, behind the ankle and crosses on the dorsal aspect of the foot. The reinforcing means may be formed integrally with the sock-like structure or, alternatively, the reinforcing means may be formed separately and subsequently inserted within the sock-like structure.

The resilience of the sock-like structure and the reinforcing means are chosen, and may be varied, in dependence upon the degree to which the patient suffers from plantarflexion. Indeed, the reinforcing means 36 can be dispensed with if sufficient resistance to plantarflexion is provided by the sock-like structure 34. It is preferred for the resilience of the reinforcing means 36, if provided, to be greater than that of the sock-like structure 34.

In this embodiment, the orthosis 32 envelops a portion of the patients lower leg which preferably includes the medial malleolus 40 (the inside of the ankle) and the lateral malleolus 42 (the outside of the ankle), the calcaneum 44 (the heel), a portion of the plantar aspect 46 of the foot (the sole of the foot) and a portion of the dorsal aspect 48 of the foot (the back of the foot). In this embodiment, the toes 49 of the foot are not enveloped by the orthosis, although they could be enveloped if desired. It is preferred that the orthosis extends beyond the medial and lateral malleoli.

The sock-like structure 34 is provided with a slit 35 which extends in a direction towards the calcaneum between the medial and lateral melleoli. In this embodiment, the slit is closable by a mechanical hook and loop fastener 50, such as velcro®. One portion of the fastener (ie. either a hook portion or a loop portion) is affixed to one side of the slit. The other portion of the fastener 50 is affixed to a strap 52 that is affixed to the other side of the slit.

Figure 4:
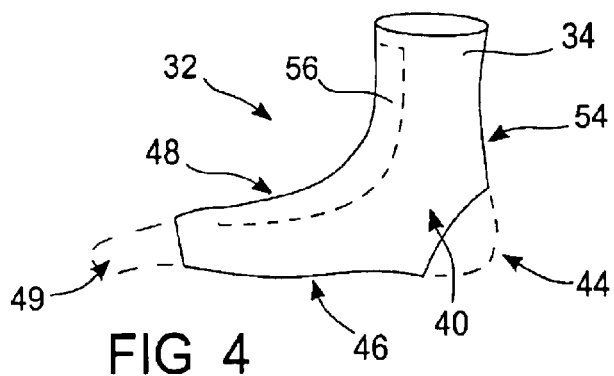
FIG. 4 is a schematic representation of an orthosis according to a second aspect of the invention.

FIG. 4 shows a second embodiment of the invention wherein the orthosis 32 is provided with a zip fastener 54, respective parts of which are secured to either side of the slit. In this embodiment, the sock-like structure 34 does not envelop the calcaneum 44 of the foot. It has been found that the orthosis 32 can be made significantly more comfortable if both the calcaneum 44 and toes 49 are not enveloped by the sock-like structure 34. In this embodiment, the reinforcing means comprises a rib 56 which extends partway along the dorsal aspect of the foot. The rib may be formed integrally with the orthosis. Alternatively, the rib may be removably insertable into a pocket provided on the dorsal aspect of the foot to allow for the stiffness of the rib, and/or the angle of support (by inserting differently shaped ribs), to be changed if desired.

The orthosis of either embodiment may be coloured so that it can be matched to the skin colour of the patient, and may be provided in a variety of different sizes and shapes. The orthosis is preferably manufactured by injection moulding. Alternatively, the orthosis may be manufactured by milling (as described below) and subsequently building up layers of the device upon a suitable cast.

The orthosis may be of a variety of different materials chosen to have a suitable resilience. For example, the orthosis could be of rubber, silicone, plastics or of any other material apparent to persons skilled in the art. Preferably the orthosis is of 35 shore silicone elastomer. The orthosis may be of a greater or lesser shore value depending upon the particular needs of the patient to which it is to be fitted. The reinforcing means may be of silicone, with a chosen shore value, or may be of any other material apparent to persons skilled in the art. The reinforcing means could be of the same material as the sock-like structure, or could be of a different material. For example, in the arrangement of FIG. 4, the rib may be of a metal.

Two suitable elastomers are sold under the product names HCR9960 and MED4035 by Nusil Technology of 1050 Cindy Lane, Carpinteria, Calif., USA. HCR9960 has a working time of approximately 12 hours and MED4035 has a shorter working time of approximately 3 to 4 hours, after which the elastomer cures. The elastomers are thermosetting and are strained through a 200 mesh screen to remove particulate contaminants.

The elastomers are supplied as A and B components which are preferably combined in equal portions on a two roll mill, or other suitable device, prior to use. A suggested sequence for blending the two components is to first soften part B on the mill and then soften part A, after which an equal weight of part B should be added to part A and then thoroughly mixed. At this stage, it is recommended to keep the temperature of the material as low as possible so as to maximise the table life of the elastomer. The mixture may then be manually fitted to a plaster cast of a patient's foot, or more preferably supplied to injection moulding apparatus to mould a suitably shaped orthosis. Curing of the blended elastomer may be accelerated by heat and can take from 3 to 4 hours. The cure may be inhibited by any ambient traces of organic rubbers and other substances and thus it is preferred for the fabrication of the orthosis to be conducted in a thoroughly cleaned area.

Figure 5:
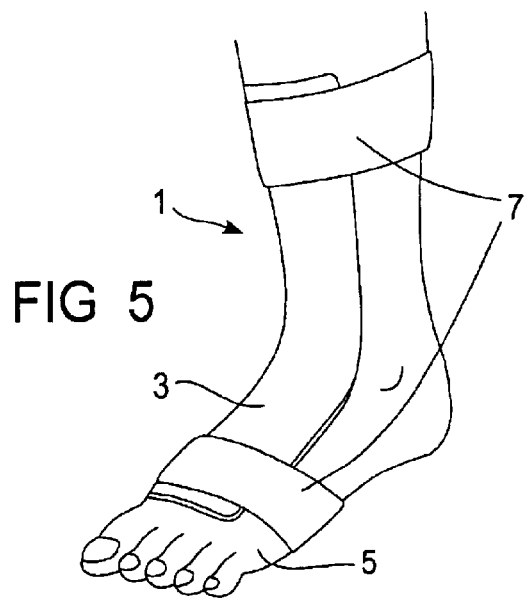
FIG. 5 is a schematic representation of an orthosis according to a third aspect of the invention.

FIG. 5 is a schematic representation of another orthosis 1 that comprises a resilient rib 3 that is locatable in use along the dorsal aspect of the patient's foot 5. As shown, the orthosis 1 extends from approximately the base of the patient's toes up to the lower portion of the patient's shin.

The rib 3 is formed of a material that is preferably relatively light-weight and resilient—such as a plastic. A preferred material is ortholene or polypropylene, but numerous other suitable materials (such as a metal, an alloy or carbon fibre or similar material for example) will be apparent to persons skilled in the art. The orthosis could be injection moulded, or for a more precise fit could be individually fitted to a patient's foot.

In order for the orthosis to benefit the patient, it must somehow be secured to the patient's foot. In the embodiment of FIG. 5, the orthosis 1 is secured to the foot 5 by way of a pair of straps 7, which in the preferred embodiment include mechanical hook-and-loop fasteners (not shown) such as velcro$^R$ that enable the straps 7 to be secured around the patients foot and lower leg respectively. Alternative fastening mechanisms, such as pop fasteners, could be provided in addition or instead of velcro$^R$. When the straps are secured about the patient's foot and lower leg, the orthosis 1 is secured to the patient's foot and plantarflexion is resisted. The arrangement of FIG. 5 is particularly advantageous for use in warmer climates as the majority of the patient's foot is not covered by the orthosis 1.

Figure 6:
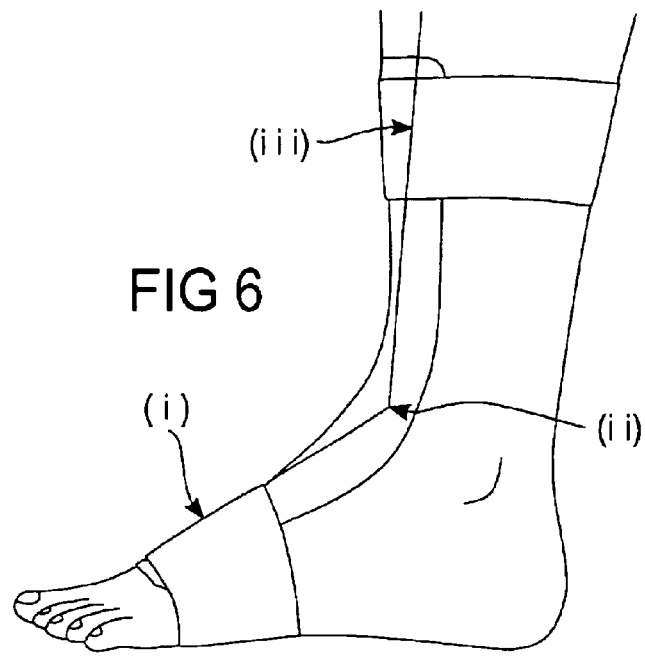
FIG. 6 is a side view of the orthosis of FIG. 5.

FIG. 6 is a side view of the orthosis 1 of FIG. 5 illustrating the points at which pressure is applied to the patient's foot by the device. As shown, the orthosis 1 applies pressure to the patient's foot at three discrete locations (i), (ii) and (iii). Application of pressure to the foot at these three locations causes plantarflexion to be resisted whilst also aiding dorsiflexion. In this way, the orthosis 1 aids the patient during all stages of the walking motion. Furthermore, the orthosis 1 shown is considerably more comfortable for the patient to wear than previously proposed devices as it does not extend beneath the foot and thus the weight of the patient does not bear upon the orthosis 1 during walking.

Figure 7:
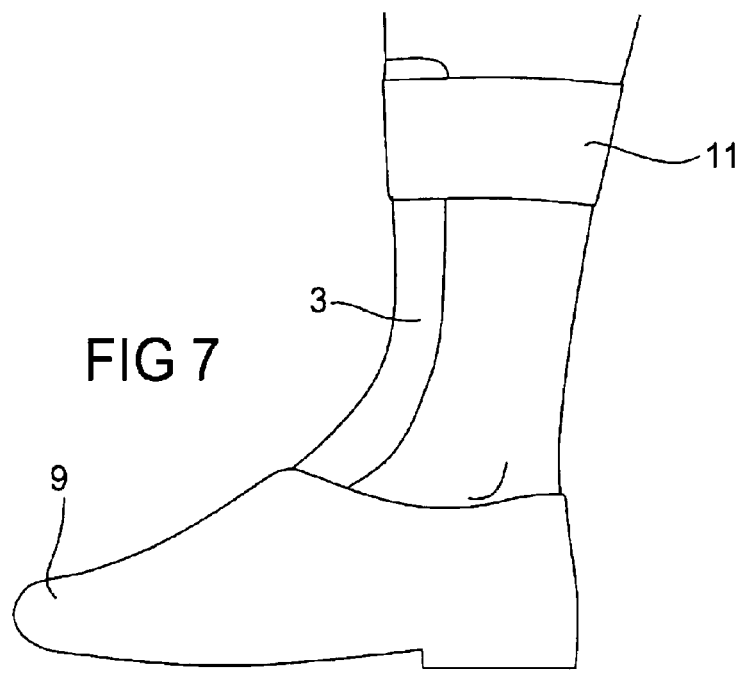
FIG. 7 is a schematic representation of an orthosis according to a fourth aspect of the invention.

A further embodiment of the invention is shown in FIG. 7. This embodiment of the invention of either embodiment is primarily designed for use in conjunction with a shoe 9, and comprises an orthosis 1 of polypropylene, for example, and a single strap 11 provided at the end of the reinforcing means closest to the patient's leg, in use. Securing the strap 11 around the patient's lower leg and inserting the foot 5 and orthosis 1 within a shoe 9 provides an orthosis that is capable of resisting plantarflexion of the patient's foot. As an alternative to providing a strap, the upper end of the orthosis could be adhered to the patients lower leg.

If the straps of the orthosis of FIG. 5 are removably attached to the rib 3, then the orthosis or FIG. 5 could be converted for use with a shoe, as shown in FIG. 7, simply by removing the lower strap.

As a further alternative that is not illustrated in the drawings, the straps could be dispensed with and the rib could then be adhered at least at the ends thereof to the Patient's lower leg and foot. The adhesive could be any adhesive suitable for bonding articles to skin.

The orthosis may be coloured so that it can be matched to the skin colour of the patient, and may be provided in a variety of different shapes and sizes.

The orthosis may be of a variety of different materials chosen to have a suitable resilience. For example, the orthosis could be of rubber, silicone, plastics, carbon fibre or of any other material apparent to persons skilled in the art. In a preferred example, the orthosis is of 35 shore silicone elastomer. The orthosis may be of a greater or lesser shore value depending upon the particular needs of the patient to which it is to be fitted.

It will be understood, of course, that the invention has been described herein by way of example only and that modifications may be made within the scope of the invention.

What is claimed is:

1. An ankle-foot orthosis configured to resist plantarflexion and assist dorsiflexion of a foot of a patient who is experiencing abnormal plantarflexion of the foot, the orthosis comprising:

a first tubular portion formed of silicone; said first tubular portion having a first end, a second end, a peripheral wall extending in a first direction from said first end to said second end, and means defining an opening in said peripheral wall;

closing means selectively operable to close said opening in said peripheral wall of said first tubular portion; and a second tubular portion formed of silicone and having a first end and a second end, at least a portion of said first end of said second tubular portion being contiguous with at least a portion of said second end of said first portion; said second tubular portion being formed integrally with said first tubular portion to extend from said first portion in a second direction transverse to said first direction;

wherein said orthosis is arranged to be worn by the patient so that said first tubular portion envelops the patient's ankle and the entire circumference of a portion of the patient's lower leg in the vicinity of the ankle, and said second tubular portion envelops at least a portion of the plantar and dorsal aspects of the patient's foot, said first and second tubular portions being resiliently flexible to thereby provide said resistance to plantarflexion and assistance with dorsiflexion of said patient's foot.

2. An orthosis according to claim 1, comprising a reinforcing means for providing a further resistance to plantarflexion of the patient's foot.

3. An orthosis according to claim 2, wherein the reinforcing means comprises a length of tape, a first end and a second end of the tape being joined together to form a figure-of-eight passing under the instep, behind the ankle and crossing on the dorsal aspect of the foot.

4. An orthosis according to claim 2, wherein the reinforcing means comprises a rib running along at least a portion of the dorsal aspect of the foot and substantially midway between the medial malleolus and the lateral malleolus.

5. An orthosis according to claim 4, wherein the rib is of plastics.

6. An orthosis according to claim 4, wherein the rib is of silicone.

7. An orthosis according to claim 6, wherein said rib is integrally formed with said first and second tubular portions.

8. An orthosis according to claim 4, wherein the rib is of polypropylene.

9. An orthosis according to claim 4, wherein the rib is of ortholene.

10. An orthosis according to claim 4, wherein the rib is of carbon fibre.

11. An orthosis according to claim 4, wherein the reinforcing means has a greater resilience than the resilience of said first and second tubular portions.

12. An orthosis according to claim 2, wherein said reinforcing means comprises a first region of said peripheral wall of said first tubular structure and a second region of a peripheral wall of said second tubular structure, wherein said first and second regions are contiguous and a resilience of said first and second tubular portion peripheral walls inside said first and second regions is greater than a resilience of said first and second tubular portion peripheral walls outside of said first and second regions.

13. An orthosis according to claim 1, wherein said opening comprises an insertion slit extending substantially midway between the medial malleolus and the lateral malleolus at the back of the ankle towards the calcaneum.

14. An orthosis according to claim 13, wherein the closing means comprises a mechanical hook and loop fastener, a set of hoops or hooks being provided on one side of the slit and a corresponding set of hooks or hoops being provided on a closure member affixed to the other side of the slit, respective hooks and loops being connectable to securely close the slit.

15. An orthosis according to claim 13, wherein the closing means comprises a zip fastener secured to opposite sides of the slit.

16. An orthosis according to claim 1, wherein said second tubular portion does not envelop the patient's toes.

17. An orthosis according to claim 1, wherein said second tubular portion does not envelop the patient's calcaneum.

18. An orthosis according to claim 1, wherein the first and second tubular portions are of 35 shore silicone elastomer.

19. An orthosis according to claim 1, wherein the orthosis is skin coloured.

20. An orthosis according to claim 1, wherein the orthosis is fabricated by injection moulding.

21. An orthosis according to claim 1, wherein the orthosis is stamped or pressed from sheet material.

22. An ankle-foot orthosis according to claim 1, wherein said first tubular portion and said second tubular portion together define a generally L-shaped cavity.

23. An ankle-foot orthosis according to claim 1, wherein said second tubular portion additionally envelops both the patient's toes and the patient's calcaneum.

24. An ankle-foot orthosis according to claim 1, wherein said first and second tubular portions are formed by manually applying a silicone elastomer to a cast of the patient's foot.

25. An ankle foot orthosis configured to resist plantarflexion and assist dorsiflexion of a foot of a patient who is experiencing abnormal plantarflexion of the foot, the orthosis comprising:

a resiliently flexible L-shaped silicone structure having a first tubular portion, and a second tubular portion that is at least partly contiguous with said first portion and is formed integrally therewith, the structure having an outer surface consisting of a first region having a first resilience and a second region with a second resilience that is greater than said first resilience;

wherein said structure is configured so that said second region overlies at least a portion of a dorsal aspect of the patient's foot and a portion of the patient's lower leg when the orthosis is worn by the patient, said second region being provided to augment the resistance to plantarflexion of the patient's foot provided by the silicone structure of the orthosis.

* * * * *